United States Patent
Matsumoto et al.

(10) Patent No.: US 8,802,622 B2
(45) Date of Patent: Aug. 12, 2014

(54) COMPOSITION FOR NASAL ADMINISTRATION AND METHOD FOR PREPARING SAME

(75) Inventors: Masaru Matsumoto, Kobe (JP); Shuji Takeda, Kobe (JP); Kyohei Nobori, Kobe (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 0 days.

(21) Appl. No.: 13/635,580

(22) PCT Filed: Mar. 18, 2011

(86) PCT No.: PCT/JP2011/056625
§ 371 (c)(1),
(2), (4) Date: Sep. 17, 2012

(87) PCT Pub. No.: WO2011/115264
PCT Pub. Date: Sep. 22, 2011

(65) Prior Publication Data
US 2013/0012439 A1    Jan. 10, 2013

(30) Foreign Application Priority Data

Mar. 19, 2010 (JP) ................. 2010-065042

(51) Int. Cl.
| | |
|---|---|
| *A61K 38/02* | (2006.01) |
| *A61K 9/14* | (2006.01) |
| *A61K 47/38* | (2006.01) |
| *A61K 38/22* | (2006.01) |
| *A61K 38/26* | (2006.01) |
| *A61K 38/29* | (2006.01) |
| *A61K 9/00* | (2006.01) |
| *A61K 38/25* | (2006.01) |
| *A61K 9/16* | (2006.01) |
| *A61K 9/48* | (2006.01) |

(52) U.S. Cl.
CPC ............. *A61K 9/0043* (2013.01); *A61K 38/29* (2013.01); *A61K 38/2242* (2013.01); *A61K 9/4866* (2013.01); *A61K 9/008* (2013.01); *A61K 38/25* (2013.01); *A61K 38/2214* (2013.01); *A61K 9/1652* (2013.01)
USPC .......... 514/1.1; 514/11.7; 514/11.8; 514/12.4; 514/9.7; 514/57

(58) Field of Classification Search
CPC . A61K 9/0043; A61K 9/1652; A61K 9/4866; A61K 9/008; A61K 38/2214; A61K 28/2242; A61K 38/25; A61K 38/29; A61K 38/22; A61K 38/26; A61K 9/14; A61K 47/38
See application file for complete search history.

(56) References Cited

U.S. PATENT DOCUMENTS

| | | |
|---|---|---|
| 7,591,999 B2 | 9/2009 | Matsuyama et al. |
| 2001/0038824 A1 | 11/2001 | Horii et al. |
| 2002/0012688 A1 | 1/2002 | Dohi et al. |
| 2006/0204448 A1 | 9/2006 | Matsuyama et al. |
| 2012/0129762 A1* | 5/2012 | Sato et al. ............... 514/2.4 |

FOREIGN PATENT DOCUMENTS

| | | |
|---|---|---|
| JP | 60-224616 | 11/1985 |
| JP | 7-206699 | 8/1995 |
| JP | 10-59841 | 3/1998 |
| JP | 2003-535042 | 11/2003 |
| WO | 2004/078211 | 9/2004 |

OTHER PUBLICATIONS

PCI-105C—Eastman cellulose esters for pharmaceutical drug delivery, from Eastman, published on Oct. 2005, pp. 1-16.*
International Search Report dated Apr. 19, 2011 mailed in PCT Application No. PCT/JP2011/056625 filed Mar. 18, 2011.
G. Norris Melville et al., "Tracheobronchial Function in Health and Disease," Respiration, 1980, pp. 329-336, vol. 40, No. 6.
"Eastman Cellulose Esters for Pharmaceutical Drug Delivery," Eastman Chemical Company, Oct. 2005, pp. 1-13.

* cited by examiner

*Primary Examiner* — Julie Ha
*Assistant Examiner* — Li Ni Komatsu
(74) *Attorney, Agent, or Firm* — Drinker Biddle & Reath LLP

(57) ABSTRACT

The invention provides a powdered composition for nasal administration, comprising a physiologically active peptide and cellulose acetate as the base, and having excellent nasal absorption for physiologically active peptides.

8 Claims, 5 Drawing Sheets

SEQUENCE LISTING

<160> NUMBER OF SEQ ID NOS: 1

<210> SEQ ID NO 1
<211> LENGTH: 22
<212> TYPE: PRT
<213> ORGANISM: Artificial
<220> FEATURE:
<223> OTHER INFORMATION: Amino acid sequence of Compound 2 (MT114)

<400> SEQUENCE: 1

```
Phe Val Pro Ile Phe Thr Tyr Gly Glu Leu Gln Arg Leu Gln Glu Lys
1               5                   10                  15

Glu Arg Asn Lys Pro Gln
            20
```

COMPOSITION FOR NASAL ADMINISTRATION AND METHOD FOR PREPARING SAME

RELATED APPLICATION DATA

This application is a §371 National Stage Application of PCT International Application No. PCT/JP2011/056625 filed Mar. 18, 2011, and claims priority under 35 U.S.C. §119 and/or §365 to Japanese Application No. 2010-065042 filed Mar. 19, 2010.

SEQUENCE LISTING

The instant application contains a sequence listing which has been submitted in ASCII format via EFS-Web and is hereby incorporated by reference in its entirety. Said ASCII copy, created on Sep. 17, 2012, is named SEQ-Z580.txt and is 1 KB in size.

TECHNICAL FIELD

The present invention relates to a cellulose acetate powder impregnated primarily with a peptide drug, and to the use of the cellulose acetate powder as a base for a composition with accelerated drug absorption through mucous membranes such as those of the nose. More specifically, the invention relates to a technique for preparing a composition with enhanced drug absorption through mucous membranes such as those of the nose, the composition being produced by mixing water and cellulose acetate with a physiologically active peptide as the active compound.

BACKGROUND ART

Currently, a large variety of physiologically active peptides or physiologically active protein preparations, such as insulin, growth hormone, atrial natriuretic peptide, calcitonin, LH-RH derivatives, parathyroid hormone and adrenocorticotropic hormone derivatives, are being marketed as pharmaceutical agents. However, because these physiologically active peptides and physiologically active proteins are inactivated by the degrading activity of proteases in the gastrointestinal tract, they cannot be easily developed as oral formulations and almost all of them are prepared in the form of parenteral formulations, mainly for injection. The administration of an injection, however, requires a hospital visit by the patient and is also painful, and therefore parenteral transmucosal formulations are desired that allow painless administration to be performed at home.

Nasal administration is one such parenteral transmucosal administration route. Here, the target is the mucous membrane of the nasal cavity, which has a structure with a developed vasoganglion, mucous membranes of the superior nasal concha, medial nasal concha and inferior nasal concha, and a wide surface area, and therefore nasal administration is expected to allow higher absorption of drugs compared to the oral, rectal and pulmonary mucous membranes. However, absorption of a peptide drug through the nasal mucosa is impeded by numerous obstacles such as low permeability through mucous membranes and degradation of physiologically active peptides by mucosal enzymes, while the bioavailability (BA), which is an index of the degree of migration of a substance into the blood, is by no means satisfactory. A variety of modifications have therefore been proposed for nasal formulations to increase absorption of peptides by nasal administration.

Conventional methods for increasing absorption of physiologically active peptides by nasal administration include 1) methods in which a substance that promotes absorption of physiologically active peptides through the nasal mucosa is added to or compounded with the composition to be administered, 2) methods in which a substance that inhibits degradation of physiologically active peptides on the nasal mucosa is added to or compounded with the composition, and 3) methods in which the residence time of the bioactive substance in the nasal mucosa is extended to increase absorption of the physiologically active peptides.

1) As regards methods in which a substance that promotes absorption of physiologically active peptides through the nasal mucosa is added to or compounded with the composition, a mucolytic agent is often used as a mucous membrane absorption accelerator. WO2004/078211 discloses a nasal administration powder formulation with improved absorption, by addition or compounding of a bioactive substance such as a cytokine, peptide hormone or growth factor, with a non-water-absorbing and poorly water-soluble cellulose derivative (such as ethylcellulose, cellulose acetate or nitrocellulose) as the base, and a mucolytic agent which might be a cysteine derivative such as N-acetyl-L-cysteine or an active SH group-containing alcohol. According to the invention described therein, when the nasal administration formulation is atomized and inhaled intranasally, the presence of the non-water-absorbing and poorly water-soluble substance serving as the base causes the physiologically active peptide and mucolytic agent to adhere and reside on the nasal mucosa, dissolving into the mucus in a trace amount, thus producing a locally high concentration solution of the physiologically active peptide and mucus solubilizer. Since it has been reported that one of the actions of N-acetyl-L-cysteine is to cleave disulfide bonds of mucus mucopolysaccharides (Non-PTL 1), the aforementioned invention takes advantage of efficient diffusion of the drug by rapid liquefaction of the mucus layer by N-acetyl-L-cysteine, as the mucolytic agent, but does not disclose any effect of the cellulose acetate, as the base, on absorption or BA of the drug.

2) As regards formulations with addition or compounding of an inhibitor of physiologically active peptide degradation, some methods involve addition or compounding of inhibitors against proteases that are present in the nasal mucosa. In Japanese Unexamined Patent Publication (kokai) No. 7-206699, there are disclosed peptide nasal and protein nasal formulations with compounding of gabexate mesylate or nafamostat mesylate, which have serine protease inhibiting activity, and it teaches that the BA is improved in these formulations.

However, safety is an issue in the methods of adding or compounding a mucolytic agent according to the solution means of 1) and the methods of adding or compounding a substance with protease inhibiting activity according to the solution means of 2), because of reported irritation of the nasal mucosa by the added or compounded substances, and therefore nasal formulation compositions are desired that are safer while exhibiting high BA for physiologically active peptides.

In methods that extend the residence time on the nasal mucosa, as according to 3), selection of the base is the most important factor. In the prior art, bases are often added that increase viscosity for greater adhesion of physiologically active peptides to the mucous membrane. Japanese Examined Patent Publication (kokoku) No. 62-42888, for example, describes a powdered composition for nasal administration that comprises a physiologically active polypeptide and a water-absorbing and water-insoluble base such as crystalline cellulose, α-cellulose or crosslinked sodium carboxymethylcellulose. A water-absorbing and water-insoluble base, when used for intranasal administration, absorbs water of the nasal mucosa and transforms the particles into a viscous liquid state such that they moderately disperse without flowing, thereby allowing the particles to reside in the adhering sections of the nasal mucosa so that the high molecular weight polypeptides satisfactorily contact the nasal mucosa, whereby absorption of the polypeptides is increased.

Japanese Unexamined Patent Publication (kokai) 10-59841 discloses using a specified amount of a water-absorbing gel-forming base such as hydroxypropylcellulose or hydroxymethylcellulose in combination with a physiologically active peptide and a water-absorbing and water-insoluble base such as crystalline cellulose, the particle sizes of the bases being 10 to 350 microns for the water-absorbing and water-insoluble base and 10 to 100 microns for the water-absorbing gel-forming base, so that the physiologically active peptide is widely dispersed throughout the nasal cavity when administered intranasally, and the gel-forming base gels and resides in the nasal cavity, resulting in an increased maximum blood concentration of the drug.

According to this prior art, the preferred bases that exhibit high BA for physiologically active peptides are water-absorbing and water-insoluble cellulose derivatives, and especially crystalline cellulose. However, water-absorbing and water-insoluble bases can produce unpleasant feelings such as itchiness in the nasal cavity, because they absorb water of the mucous membrane after atomized in the nasal cavity, and therefore the nasal formulation has been problematic in terms of compliance.

PRIOR ART LITERATURE

Patent literature

PTL 1: WO2004/078211
PTL 2: Japanese Unexamined Patent Publication (kokai) No. 7-206699
PTL 3: Japanese Unexamined Patent Publication (kokai) No. 10-59841
PTL 4: Japanese Examined Patent Publication (kokoku) No. 62-42888

Non-Patent Literature

Non-PTL 1: Melville G N et al. Respiration 1980; 40(6):329-336

SUMMARY OF THE INVENTION

Problems to be Solved by the Invention

It is an object of the invention to provide a powdered composition for nasal administration employing a base that increases absorption of physiologically active peptides.

Means for Solving the Problems

The present inventors have conducted diligent research on selection of substances to serve as bases, methods of formulation, and distribution of physiologically active peptides in base particles, with the aim of developing a nasal formulation with increased BA for physiologically active peptides. In the course of such research, the present inventors considered selection of the base to be of greatest importance, and focused on cellulose acetate based on the hypothesis that for a formulation to exhibit high BA for a physiologically active peptide in nasal administration, it is a desirable and necessary property for the base to satisfy the conditions of suitable retentivity and water absorption in the nasal mucosa and excellent timing for retention and release of the physiologically active peptide.

A formulation administered to the nasal mucosa resides in the nasal cavity for about 10 to 15 minutes, and is gradually drained toward the back of the nasal cavity by mucociliary clearance. One method in the prior art for preparing nasal formulations for physiologically active peptides is a solid mixing method, in which the dried base and physiologically active peptide are combined, generally with the aim of stabilizing the physiologically active peptide as the main active compound. In such formulation methods, however, the physiologically active peptide merely adheres to the particle surfaces of the base, and when the formulation is nasally administered the physiologically active peptide on the base surface rapidly diffuses into the nasal mucus, making it difficult to maintain a high concentration of the physiologically active peptide at the site of administration. The present inventors have demonstrated that 1) addition of an appropriate amount of water to cellulose acetate, which has low water absorption, can produce a cellulose acetate formulation wherein the physiologically active peptide is also held inside the base particles, that 2) a formulation wherein the physiologically active peptide is also held inside the particles exhibits higher BA when intranasally administered, compared to the BA with a nasal formulation prepared by solid mixing of the physiologically active peptide and base, and that 3) the amount of water added with respect to the cellulose acetate weight in this method is a very important factor for obtaining high BA, and we have completed this invention as a powdered composition for nasal administration that is efficient for physiologically active peptides.

The present invention therefore encompasses the following.

1) A composition for nasal administration comprising a physiologically active peptide and cellulose acetate as a base.
2) The composition according to 1), wherein the physiologically active peptide is impregnated into the base.
3) The composition according to 1) or 2), wherein the acetylation degree of the cellulose acetate is 32-40%.
4) The composition according to any one of 1) to 3), wherein the physiologically active peptide is a peptide with a molecular weight of no greater than 20,000.
5) The composition according to 4), wherein the physiologically active peptide is human glucagon-like peptide-1 (GLP-1), human parathyroid hormone, human parathyroid hormone 1-34 (hPTH (1-34)), human motilin, human motilin derivative, human ghrelin, human atrial natriuretic peptide, brain natriuretic peptide (BNP) or C-type natriuretic peptide (CNP).
6) A method for preparing a composition according to any one of 1) to 5), wherein the powdered composition for nasal administration is produced by mixing a physiologically active peptide, cellulose acetate and water and then drying the mixture.
7) The method according to 6), wherein the amount of water used in the mixture of the physiologically active peptide, cellulose acetate and water is at least 20 wt % with respect to the cellulose acetate.
8) The method according to 7), wherein the amount of water used in the mixture of the physiologically active peptide, cellulose acetate and water is at least 20% and no greater than 250% with respect to the cellulose acetate.

9) The method according to 8), wherein the amount of water used in the mixture of the physiologically active peptide, cellulose acetate and water is at least 100% and no greater than 250% with respect to the cellulose acetate.

Effect of the Invention

Since it is a preferred property of a base to have suitable retentivity in the nasal mucosa in order for a formulation to exhibit high BA for a physiologically active peptide in a composition for nasal administration, it is necessary to satisfy the conditions of being water-insoluble, having water absorption that is moderate but lower than crystalline cellulose, and having excellent timing for retention and release of the physiologically active peptide. By using cellulose acetate as a base satisfying these conditions according to the invention, a safer composition, with excellent feel during use and increased absorption of physiologically active peptides, may be provided without requiring other added or compounded substances.

MODE FOR CARRYING OUT THE INVENTION

Figure 1:
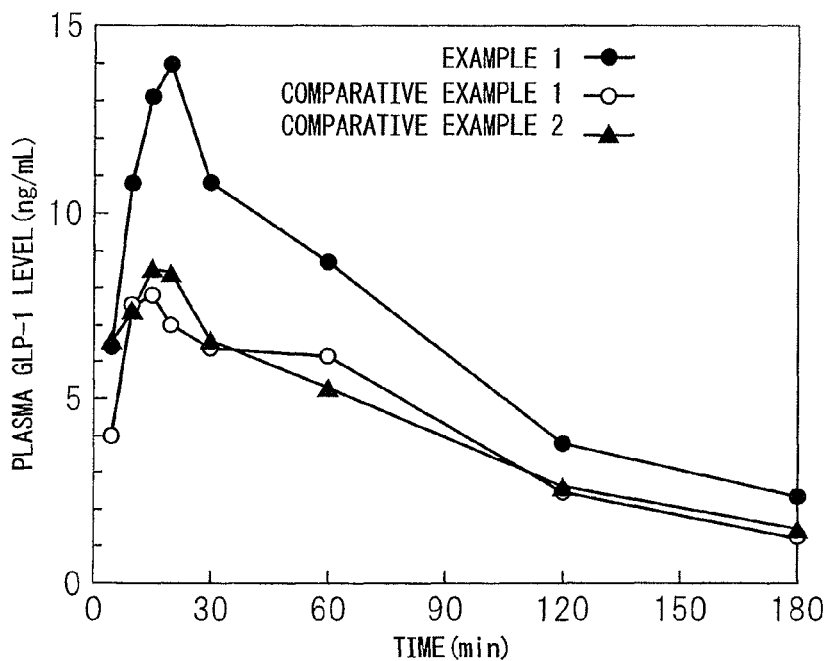
FIG. 1 shows the time-dependent change in blood plasma GLP-1 levels of a mixed solution composition of GLP-1 and cellulose acetate (Example 1), a mixed solid composition of GLP-1 and cellulose acetate (Comparative Example 1) and a mixed solution composition of GLP-1 and crystalline cellulose (Comparative Example 2), after nasal administration to cynomolgus monkeys.

The present invention provides a powdered composition for nasal administration produced by mixing cellulose acetate as a base, a physiologically active peptide and water and subsequently drying the mixture, whereby a high BA is obtained so that the physiologically active peptide exhibits sufficient activity in the body.

The composition of the invention utilizes the water-absorbing effect of the cellulose acetate base to impregnate the physiologically active peptide into the base, thereby allowing the physiologically active peptide to be retained not only on the surface but also in the interior of the base surface. The composition can be produced by mixing a physiologically active peptide, cellulose acetate and water and then drying the mixture. The order for mixing of the physiologically active peptide, cellulose acetate and water is not restricted, and it may be any of the following. 1) Addition of water to a mixture of the physiologically active peptide and cellulose acetate. 2) Dissolution of the physiologically active peptide in water followed by addition of cellulose acetate and mixing. 3) Mixture of the cellulose acetate and water, followed by addition of the physiologically active peptide and mixing. The mixture is then dried. According to the invention, mixture of the base and physiologically active peptide may be accomplished by hand, using a high-speed stirrer, using a revolving/rotating stirrer or using a biaxial planetary system mixing kneader, any of which may be used without limitations.

Because of the cellulose acetate base, atomization or inhalation of the composition of the invention through a mucous membrane such as in the nasal cavity allows it to adhere and reside on the mucous membrane. In addition, the cellulose acetate particles residing on the mucous membrane absorb slight amounts of mucus from the mucous membrane surface, which dissolve the physiologically active peptide being held in the cellulose acetate, thereby creating a locally high concentration of the physiologically active peptide. The concentration gradient of the physiologically active peptide in this state is utilized so that the physiologically active peptide efficiently passes through the mucous membrane and reaches the adjacent vasoganglion, to increase transmucosal absorption of the physiologically active peptide.

The cellulose acetate for the invention is a semisynthetic polymer generally obtained by acetic acid esterification of the natural polymer cellulose. Cellulose is a long-chain natural polysaccharide comprising β-1,4-glucoside bonded glucose. When the hydroxyl groups of cellulose are modified for esterification or etherification, it becomes thermoplastic or water-soluble, or plastic in organic solvents, and is thus easily moldable. For the water-absorbing properties of a cellulose derivative, introduction of methyl groups, for example, into the cellulose molecules prevents hydrogen bonding between the hydroxyl groups of the cellulose, imparting a hydrating property to the cellulose molecules and thereby improving the water-solubility. That is, cellulose acetate with different properties including water-absorbing properties will be present, depending on the degree of acetylation (the acetyl group content) of the cellulose hydroxyl groups and differences in the polymerization degree of the cellulose chains. Cellulose acetate with any acetyl group content or polymerization degree may be used so long as the object of the invention is achieved, but from the viewpoint of obtaining suitable hydroaffinity and water absorption properties, it is preferred to use cellulose acetate with an acetyl group content of 32-40%.

A commercially available powder product of cellulose acetate may be used, or a powder product may be further processed and used with a desired particle size or shape.

The method for processing the cellulose acetate base may be an appropriate common fine particle-forming method, and for example, it may be a physical grinding method such as jet mill grinding, hammer mill grinding, rotary ball mill grinding, vibrating ball mill grinding, bead mill grinding, shaker mill grinding, rod mill grinding, tube mill grinding or the like, a crystallization method in which the cellulose acetate is first dissolved in a solvent and then subjected to temperature change and solvent composition alteration for crystallization, and then centrifugal separation or filtration to collect the crystals, or a spray dry method in which the cellulose acetate is first dissolved in a solvent and then a spray nozzle is used for atomization in a dry spray drier chamber, and the solvent in the atomized solution is rapidly evaporated off.

The cellulose acetate may be treated by sifting, gravity-settling classification, centrifugal classification or inertial force classification with an airflow, to standardize the particle size range and minimize particle size variation. The particle size can be measured using, for example, a laser diffraction particle size distribution analyzer, a sieving classifier or an image analysis particle size meter.

The mean particle size of the cellulose acetate will differ depending on the type of physiologically active peptide in the composition, but usually it will be in the range of 0.1 to 1000 μm, and it is preferably in the range of 1 to 500 μm and more preferably in the range of 20 to 200 μm, for wide diffusion in the nasal cavity.

The cellulose acetate holding the physiologically active peptide of the invention may be obtained, for example, by mixing an aqueous solution of the physiologically active peptide, dissolved in water in a desirable amount, with cellulose acetate and drying the mixture. The drying may also be performed with addition of a desirable amount of water either after the powdered physiologically active peptide and cellulose acetate have been mixed, or during the mixing. The method for drying the cellulose acetate powder to which the physiologically active peptide-containing water has been added may be any method that permits the object of the invention to be achieved, but it is preferably vacuum drying or freeze-drying.

According to the invention, it is preferred to use water during mixing of the physiologically active peptide and the cellulose acetate base. A water-miscible solvent may also be added, which does not dissolve the cellulose acetate. For example, alcohols, acetonitrile, acetone or the like may be mixed with the water in any desired proportion that satisfies the aforestated conditions.

According to the invention, the amount of mixing water is preferably between 0.2- and 500-fold (20-500%) and more preferably between 0.2- and 2.5-fold (20-250%) with respect to the cellulose acetate weight, while a range of 1- to 2.5-fold (100%-250%) is especially preferred from the viewpoint of facilitating handling of the composition during mixing.

After the physiologically active peptide-retaining cellulose acetate powder has been prepared, a commonly known method may be used for further grinding and sifting to the desired particle size.

According to the invention, the cellulose acetate base may be used in combination with any desired physiologically active peptide as the active compound. A physiologically active peptide, for the purpose of the invention, is any substance exhibiting a desired effect in vivo, without any particular restrictions. However, physiologically active peptides with molecular weights of no greater than 20,000 are preferred for combination with cellulose acetate, because they have relatively high absorption through mucous membranes. Peptides whose mucous membrane permeability may be accelerated according to the invention include a wide variety of peptide drugs, and especially human glucagon-like peptide-1 (GLP-1), human parathyroid hormone (hPTH) and its N-terminal fragment hPTH (1-34), human motilin, human ghrelin, human atrial natriuretic peptide, brain natriuretic peptide (BNP), C-type natriuretic peptide (CNP), human insulin, leptin, resistin, glucagon, relaxin, galanin, gastrin, apelin, selectin, calcitonin, adrenomedullin, amylin, humanin, thymosin, endorphin, endomorphin, nocistatin, enkephalin, neuropeptide Y, neuropeptide S, neuromedin U, angiotensin, endoserine, guanylin, salusin, urotensin, oxytocin, vasopressin, neurophysin, melanocyte-stimulating hormone, urocortin, lipotropin, luteinizing hormone-releasing hormone, mestatin, prolactin-releasing peptide, somatostatin, cortistatin, thyroid stimulating hormone-releasing hormone, substance P, neurokinin, endokinin, neurotensin, neuromedin N, obestatin, orexin, insulin-like growth factor-1 (IGF-1), melanin-concentrating hormone, corticotropin-releasing hormone, exendin-4, katacalcin, cholecystokinin, corticotropin, melanotropin, neuromedin C, copeptin, pituitary adenylate cyclase-activating polypeptide (PACAP), peptide YY, thyroliberin, and physiologically active peptide derivatives of the foregoing, are expected to have increased BA by combination with cellulose acetate in comparison to other bases. Here, "derivative" refers to any physiologically active peptide having the natural peptide sequence with a substitution, and especially a conservative substitution, and/or a deletion or addition of one or few naturally occurring amino acids. The peptide used may be a commercially available product, or it may be one produced by chemical synthesis, or for a peptide comprising naturally-occurring L-amino acids, by recombinant DNA technology or a combination of the foregoing.

The physiologically active peptide in the composition of the invention is absorbed into the body through blood vessels under the nasal mucosa immediately after administration and has a rapid drug effect expression, and therefore the short onset time until the effect is exhibited after drug administration allows optimal use of clinically useful physiologically active peptides.

The mixing ratio of the cellulose acetate and physiologically active peptide in the composition of the invention will depend on various factors including the physiologically active peptide type and the dosage form of the composition, but the physiologically active peptide may be used in the range of 0.01-50 wt % of the entire composition, and the cellulose acetate powder may be used in the range of 50-100 wt % of the entire composition.

The dosage for atomization or inhalation of the composition of the invention will usually be 0.1-500 mg/administration, and preferably 1-100 mg/administration. Since the composition of the invention exhibits increased BA despite such small dosages, even physiologically active peptides that require relatively large in vivo absorption (about 1 mg/patient/administration) for expression of physiological action can be absorbed in the necessary amounts for their drug effects.

The composition of the invention increases BA only by combination of the physiologically active peptide with cellulose acetate as the base. However, an excipient, preservative, antiseptic agent or the like may also be added, so long as the object of the invention is not adversely affected. There may also be used talc, stearic acid, salts such as sodium or calcium salts, and Carplex®, as lubricants, starch or dextrin as binders, citric acid or glycine as pH regulators, ascorbic acid and the like as preservatives, paraoxybenzoic acid esters, benzalkonium chlorides, phenol and chlorobutanol as antiseptic agents, and menthol and citrus flavors as odor correctives.

In order to minimize variation in the level of the bioactive substance administered by a single atomization or inhalation, the cellulose acetate used as the base may be further added as an excipient.

For the same purpose, appropriate amounts of other solid components may be added in addition to the physiologically active peptide and cellulose acetate, so long as the mucous membrane is not adversely affected and absorption of the physiologically active peptide is not impeded.

The composition of the invention may be administered by atomization in the nasal cavity, using a prescribed amount of air or a gas that does not have adverse effects on the human body (air, nitrogen gas, argon gas, carbon dioxide gas, a fluorocarbon substitute, or the like).

The method of atomization may employ any general transnasal or transpulmonary delivery device, and for example, the composition of the invention may be filled into a metered-dose pressurized delivery device and atomized into the nasal cavity or trachea in metered doses, or the composition of the invention may be filled into capsule units that are inserted into a pressurized delivery device to be atomized through a perforation when required, and sprayed into the nasal cavity or trachea with air or a gas that has no adverse effects on the human body.

When the composition is to be administered into the nasal cavity, this can be accomplished by aspiration alone, and the composition may be filled into a fixed-volume capsule or blister pack unit, and inserted directly into an aspirator when necessary and aspirated, to allow the composition to reach the nasal cavity.

The composition of the invention is not limited to nasal administration and may instead by used for transpulmonary administration, transpharyngeal administration or transbronchial administration, using ordinary delivery devices suited for the method of administration.

EXAMPLES

The present invention will now be described in greater detail by examples, with the understanding that the scope of the invention is not limited by these examples.

(Experiment Method 1)
Absorption Test with Composition for Nasal Administration Using Cynomolgus Monkeys
1-1. Preparation of Composition for Nasal Administration The physiologically active polypeptides used were glucagon-like peptide (GLP-1), human parathyroid hormone 1-34 (hPTH (1-34)) and a motilin derivative. Compositions for nasal absorption containing each peptide were prepared by the methods described in Examples 1 to 10 and Comparative Examples 1 to 9. Each peptide was filled into a #2 gelatin capsule in an amount of approximately 500 µg. GLP-1 and hPTH (1-34) were produced by publicly-known gene recombination techniques and used for the test. Motilin is a peptide consisting of 22 amino acids, and the motilin derivative for the invention was a peptide with the following sequence, produced by known gene recombination techniques. Phe-Val-Pro-Ile-Phe-Thr-Tyr-Gly-Glu-Leu-Gln-Arg-Leu-Gln-Glu-Lys-Glu-Arg-Asn-Lys-Pro-Gln (I) (SEQ ID NO: 1)

1-2. Atomization Method

Cynomolgus monkeys with body weights of approximately 6 kg were used (Hamri Co., Ltd.). The monkeys were starved from the day prior to the test, and restrained in a monkey chair on the day of the test. An intranasal atomizer (Hitachi Automotive Systems, Ltd.) was used for the administration. One capsule was set in nasal formulation device and intranasally administered to the cynomolgus monkeys by pumping 5 times in synchronization with intake. Blood was sampled from the radial cutaneous vein at 5, 10, 15, 20, 30, 60, 120 and 180 minutes after administration.

1-3. Blood Treatment Method
1-3-1. Blood Treatment After Administration of GLP-1 Composition for Nasal Administration A disposable injection needle was mounted on a heparin sodium-wetted glass syringe for blood sampling. Immediately after blood sampling, a 1/100 volume of 10% $EDTA.2Na.2H_2O$ with physiological saline and a 1/100 volume of DPP IV inhibitor were added, and then the mixture was cooled on ice and centrifuged (4° C.) to obtain the blood plasma.

1-3-2. Blood Treatment After Administration of hPTH (1-34) Composition for Nasal Administration A disposable injection needle was mounted on a heparin sodium-wetted glass syringe for blood sampling. Immediately after blood sampling, a 1/100 volume of 10% $EDTA.2Na.2H_2O$ was physiological saline was added, and then the mixture was cooled on ice and centrifuged (4° C.) to obtain the blood plasma. An aprotinin solution was added at 1/10 of the volume of the obtained plasma, and the mixture was stirred.

1-3-3. Blood Treatment After Administration of Motilin Derivative Composition for Nasal Administration A disposable injection needle was mounted on a heparin sodium-wetted glass syringe for blood sampling. Immediately after blood sampling, a 1/100 volume of 10% $EDTA.2Na.2H_2O$ was physiological saline was added, and then the mixture was cooled on ice and centrifuged (4° C.) to obtain the blood plasma. An aprotinin solution was added at 1/10 of the volume of the obtained plasma, and the mixture was stirred.

1-4. Measurement of Plasma Drug Levels

The drug levels in the sampled blood plasma were measured in the following manner.

1-4-1. Measurement of Plasma GLP-1 Level

A GLP-1 ELISA kit (Linco) was used to measure the blood plasma GLP-1 level by an enzyme-linked immunoassay method (ELISA). Treatment was conducted according to the kit protocol, and the absorbance at 355 nm/460 nm was measured. The BA was calculated by comparing the plasma level/time area under the curve (AUC) after nasal administration, with the AUC after intravenous administration of GLP-1 dissolved in a 5% mannitol solution.

1-4-2. Measurement of Blood Plasma hPTH (1-34) Level

A radioimmunoassay method (RIA) was used to measure the blood plasma hPTH (1-34) level. After adding anti-PTH antibody to the blood plasma specimen, [$^{125}$I-Tyr34]hPTH (1-34) was added and competition reaction was conducted. A secondary antibody was then added, the hPTH (1-34)-binding anti-PTH antibody was precipitated, and the radioactivity in the precipitated fraction after supernatant separation was measured with a γ-counter (Packard). The BA was calculated by comparing the plasma level/time area under the curve (AUC) after nasal administration, with the AUC after intravenous administration of PTH dissolved in a 5% mannitol solution.

1-4-3. Measurement of Plasma Motilin Derivative Level

The motilin derivative blood plasma level was measured by a radioimmunoassay method (RIA) using anti-human motilin antibody. Specifically, anti-human motilin antibody was added to the blood plasma specimen, and then $^{125}$I-human motilin was added for competition reaction. A secondary antibody was then added, the human motilin binding to the anti-human motilin antibody was precipitated, and the radioactivity in the precipitated fraction after supernatant separation was measured with a γ-counter (Perkin-Elmer). The BA was calculated by comparing the plasma level/time area under the curve (AUC) after nasal administration, with the AUC after intravenous administration of motilin derivative dissolved in a 5% mannitol solution.

Cellulose acetate (CA398 by Eastman Chemical Company, acetyl group content: 39.8%) was ground using a hammer mill (ACM-15H by Hosokawa Micron Group). The ground cellulose acetate was sieved using a reduced-pressure aspirated sieving machine (200LS-N by Hosokawa Micron Group), and the 40-100 µm fraction was obtained. Cellulose acetate of this fraction was used as the base for the test, unless otherwise specified.

Crystalline cellulose (CEOLUS PH-101 by Asahi Kasei Chemicals Corp.) was also sieved with a reduced-pressure aspirated sieving machine in the same manner, and the 40-100

μm fraction was obtained. Crystalline cellulose of this fraction was used as the base for the test, unless otherwise specified.

Example 1

A 100 mg portion of GLP-1 was dissolved in 4 mL of purified water. After kneading 4 g of cellulose acetate with the solution in a beaker using a spatula, the mixture was dried to obtain a composition (GLP-1 solution mixture composition).

Comparative Example 1

To a mortar there were added 100 mg of GLP-1 and 4 g of cellulose acetate. A cycle of mixing with a pestle for 30 seconds followed by passive cooling for 30 seconds was repeated 3 times to obtain a composition (GLP-1 solid mixture composition).

Comparative Example 2

A 100 mg portion of GLP-1 was dissolved in 4 mL of purified water. This solution was kneaded with 4 g of crystalline cellulose in a beaker using a spatula, and the mixture was dried to obtain a composition (GLP-1 crystalline cellulose composition).

Nasal absorption in monkeys was evaluated according to Experiment Method 1, for the compositions obtained in Example 1, Comparative Example 1 and Comparative Example 2. The results are shown in FIG. 1. The BA values for the compositions of Example 1, Comparative Example 1 and Comparative Example 2 were 57.9%, 48.4% and 38.2%, respectively. The GLP-1 solution mixture composition (Example 1) exhibited satisfactory absorption compared to the GLP-1 solid mixture composition (Comparative Example 1) or GLP-1 crystalline cellulose composition (Comparative Example 2).

Example 2

A 100 mg portion of hPTH (1-34) was dissolved in 4 mL of purified water. After kneading 4 g of cellulose acetate with the solution in a beaker using a spatula, the mixture was dried to obtain a composition (hPTH solution mixture composition).

Comparative Example 3

To a mortar there were added 100 mg of hPTH (1-34) and 4 g of cellulose acetate. A cycle of mixing with a pestle for 30 seconds followed by passive cooling for 30 seconds was repeated 3 times to obtain a composition (hPTH solid mixture composition).

Comparative Example 4

A 100 mg portion of hPTH (1-34) was dissolved in 4 mL of purified water. This solution was kneaded with 4 g of crystalline cellulose in a beaker using a spatula, and the mixture was dried to obtain a composition (hPTH crystalline cellulose composition).

Figure 2:
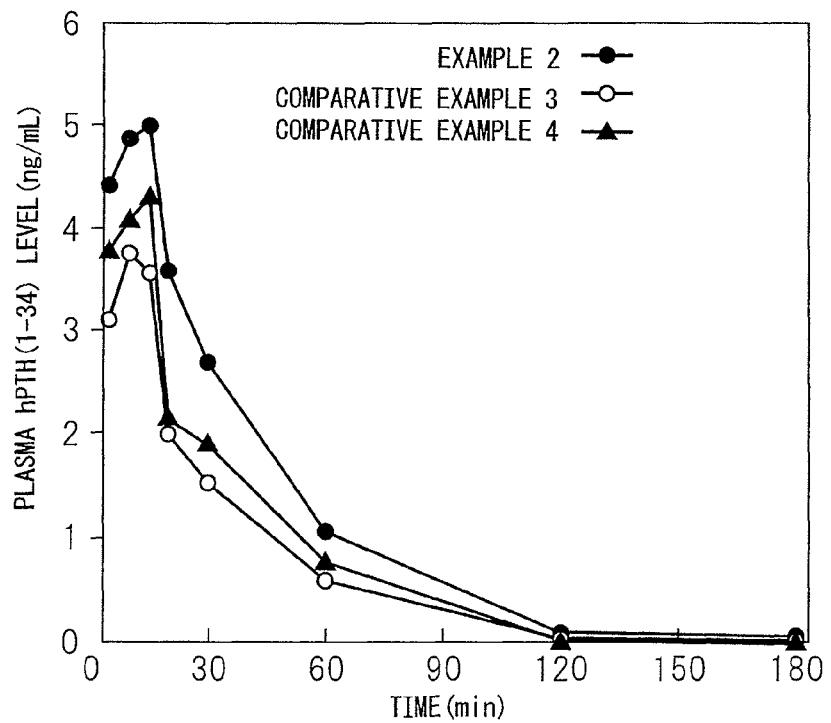
FIG. 2 shows the time-dependent change in blood plasma PTH levels of a mixed solution composition of hPTH (1-34) and cellulose acetate (Example 2), a mixed solid composition of hPTH (1-34) and cellulose acetate (Comparative Example 3) and a mixed solution composition of hPTH (1-34) and crystalline cellulose (Comparative Example 4), after nasal administration to cynomolgus monkeys.

Nasal absorption in monkeys was evaluated according to Experiment Method 1, for the compositions obtained in Example 2, Comparative Example 3 and Comparative Example 4. The results are shown in FIG. 2. The BA values for the compositions of Example 2, Comparative Example 3 and Comparative Example 4 were 3.8%, 2.8% and 2.3%, respectively. The hPTH solution mixture composition (Example 2) exhibited satisfactory absorption compared to the hPTH solid mixture composition (Comparative Example 3) or hPTH crystalline cellulose composition (Comparative Example 4).

Example 3

A 100 mg of motilin derivative was dissolved in 4 mL of purified water. After kneading 4 g of crystalline cellulose with the solution in a beaker using a spatula, the mixture was dried to obtain a composition (motilin derivative solution mixture composition).

Comparative Example 5

To a mortar there were added 100 mg of motilin derivative and 4 g of crystalline cellulose. A cycle of mixing with a pestle for 30 seconds followed by passive cooling for 30 seconds was repeated 3 times to obtain a composition (motilin derivative solid mixture composition).

Comparative Example 6

A 100 mg of motilin derivative was dissolved in 4 mL of purified water. This solution was kneaded with 4 g of crystalline cellulose in a beaker using a spatula, and the mixture was dried to obtain a composition (motilin derivative crystalline cellulose composition).

Figure 3:
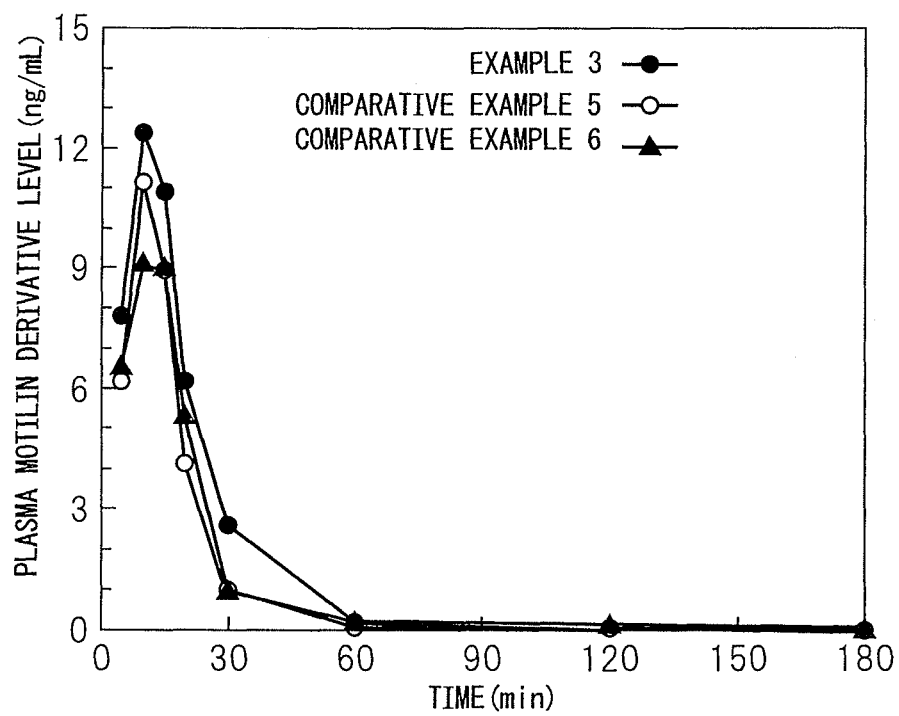
FIG. 3 shows the time-dependent change in blood plasma motilin derivative levels of a mixed solution composition of motilin derivative and cellulose acetate (Example 3), a mixed solid composition of motilin derivative and cellulose acetate (Comparative Example 5) and a mixed solution composition of motilin derivative and crystalline cellulose (Comparative Example 6), after nasal administration to cynomolgus monkeys.

Nasal absorption in monkeys was evaluated according to Experiment Method 1, for the compositions obtained in Example 3, Comparative Example 5 and Comparative Example 6. The results are shown in FIG. 3. The BA values for the compositions of Example 3, Comparative Example 5 and Comparative Example 6 were 4.6%, 4.0% and 3.3%, respectively. The motilin derivative solution mixture composition (Example 3) exhibited more satisfactory absorption than the motilin derivative solid mixture composition (Comparative Example 5) or motilin derivative crystalline cellulose composition (Comparative Example 6).

Example 4

After mixing 300 mg of motilin derivative and 12 g of cellulose acetate with a high-speed agitating granulator (PalmXer by Higuchi, Inc.), 2.4 mL of purified water was added dropwise while stirring for kneading. The mixture was then dried to obtain a composition.

Example 5

A 300 mg of motilin derivative was dissolved in 12 mL of purified water. Using a planetary stirrer (PRIMIX, HIVIS MIX), the solution was gradually added to 12 g of cellulose acetate, and the mixture was kneaded and dried to obtain a composition.

Example 6

A 25 mg of motilin derivative was dissolved in 2.5 mL of purified water. After kneading 1 g of cellulose acetate with the solution in a beaker using a spatula, the mixture was dried to obtain a composition.

Example 7

A 12.5 mg of motilin derivative was dissolved in 2.5 mL of purified water. After kneading 0.5 g of cellulose acetate with the solution in a beaker using a spatula, the mixture was dried to obtain a composition.

Comparative Example 7

To a mortar there were added 10 mg of motilin derivative and 0.4 g of cellulose acetate. A cycle of mixing with a pestle for 30 seconds followed by passive cooling for 30 seconds was repeated 3 times to obtain a composition.

Comparative Example 8

To a mortar there were added 50 mg of motilin derivative and 2 g of cellulose acetate. A cycle of mixing with a pestle for 30 seconds followed by passive cooling for 30 seconds was repeated 3 times, and then 0.1 mL of purified water was added, mixed therewith and dried to obtain a composition.

Figure 4:
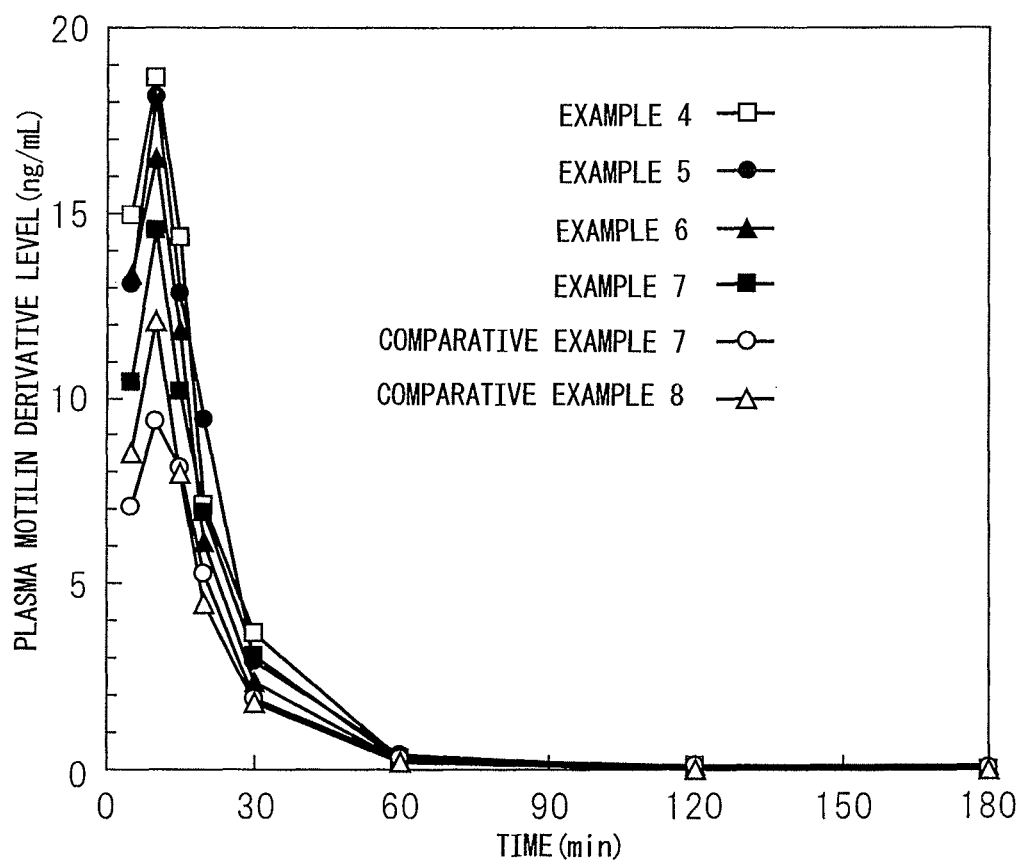
FIG. 4 shows the time-dependent change in blood plasma motilin derivative levels of a mixed solution composition of motilin derivative and cellulose acetate mixed in purified water at a cellulose acetate concentration of 25-500 wt % (Examples 4 to 7), a mixed solution composition of motilin derivative and cellulose acetate mixed with purified water at a cellulose acetate concentration of 5% wt % (Comparative Example 7), and a mixed solid composition of motilin derivative and cellulose acetate (Comparative Example 8), after nasal administration to cynomolgus monkeys.

All of the compositions of Examples 4 to 7 and Comparative Examples 7 and 8 had a cellulose acetate weight of 1:40 with respect to the motilin derivative, and were mixed with varying amounts of water and then dried, to obtain the compositions for nasal administration. Each composition was nasally administered to cynomolgus monkeys at approximately 500 μg for each dosage of motilin derivative, and blood was periodically sampled. The results are shown in FIG. 4 and Table 1. The compositions of Examples 4 to 7 had BA values of 5% or greater, while the compositions of Comparative Examples 7 and 8 had BA values of no greater than 4%. This demonstrated that the amount of water added is preferably at least 20% with respect to the cellulose acetate.

TABLE 1

Water amounts and BA values for mixtures of drug agents and cellulose acetate

| | Agent:Cellulose acetate | Addition of water to cellulose acetate (w/w) | BA |
|---|---|---|---|
| Comp. Example 7 | 1:40 | 0% | 3.6% |
| Comp. Example 8 | 1:40 | 5% | 3.6% |
| Example 4 | 1:40 | 20% | 5.4% |
| Example 5 | 1:40 | 100% | 5.0% |
| Example 6 | 1:40 | 250% | 5.6% |
| Example 7 | 1:40 | 500% | 4.8% |

Example 8

Cellulose acetate with a different acetyl group content than the aforementioned cellulose acetate (acetyl group: 32.0%, Eastman Chemical Company) was used as the base to prepare a composition. The cellulose acetate was ground with a pin mill (sample mill by Nara Machinery Co., Ltd.). The ground cellulose acetate was sieved using a reduced-pressure aspirated sieving machine (200LS-N by Hosokawa Micron Group), and the 40-100 μm fraction was obtained. A solution of 0.5 g of the obtained cellulose acetate powder and 12.5 mg of the motilin derivative in 0.5 mL of purified water was added to a beaker, and after using a spatula for kneading, the mixture was dried to obtain a composition.

Figure 5:
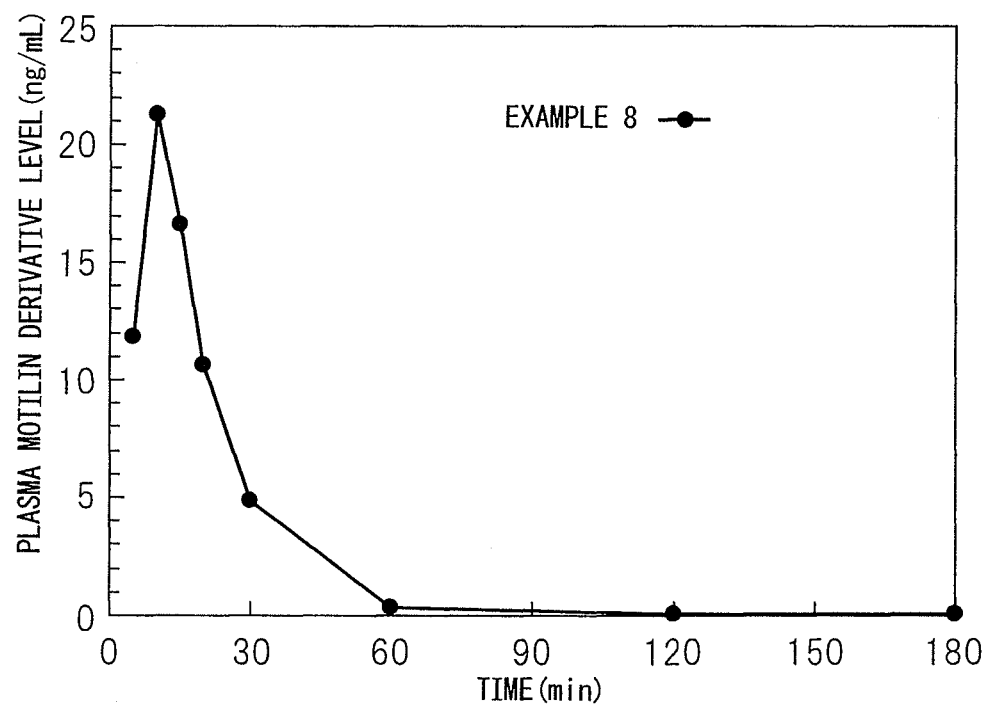
FIG. 5 shows the time-dependent change in blood plasma motilin derivative levels of a mixed solution composition of motilin derivative and cellulose acetate with an acetyl group content of 32.0% (Example 8), after nasal administration to cynomolgus monkeys.

Nasal absorption in monkeys was evaluated according to Experiment Method 1, for the powder composition using cellulose acetate with an acetyl group content of 32.0%, obtained in Example 8, as the base. The results are shown in FIG. 5. The BA values for the composition of Example 8 was 6.7%. It was thus demonstrated that a satisfactory BA is exhibited when using cellulose acetate with an acetyl group content of 32.0% or 39.8%.

Example 9

The motilin derivative used in Example 3 and other examples was fluorescently labeled in the following manner. First, 100 mg of the motilin derivative (compound MT114) was dissolved in phosphate buffer (pH 8.3), and 10 mg of Fluorescein-5-EX N-hydroxysuccinimide ester (Sigma-Aldrich Corp.) dissolved in dimethyl sulfoxide was added and mixed therewith. Following the reaction, Sep-Pak Plus CM Cartridges (Waters) and Sep-Pak Plus C18 Environmental Cartridges (Waters) were used for solid-phase extraction from the obtained solution, and freeze-drying was performed to obtain 37 mg of a fluorescent-labeled motilin derivative. Next, the motilin derivative and the fluorescent-labeled motilin derivative were mixed in a proportion of 50:1, and after dissolving in water, the solution was freeze-dried and used for preparation of compositions for Example 10 and Comparative Example 9.

Example 10

The fluorescent-labeled motilin derivative prepared in Example 9 was used to prepare a composition in the same manner as Example 5.

Comparative Example 9

The fluorescent-labeled motilin derivative prepared in Example 9 was used to prepare a composition in the same manner as Comparative Example 7.

Figure 6:
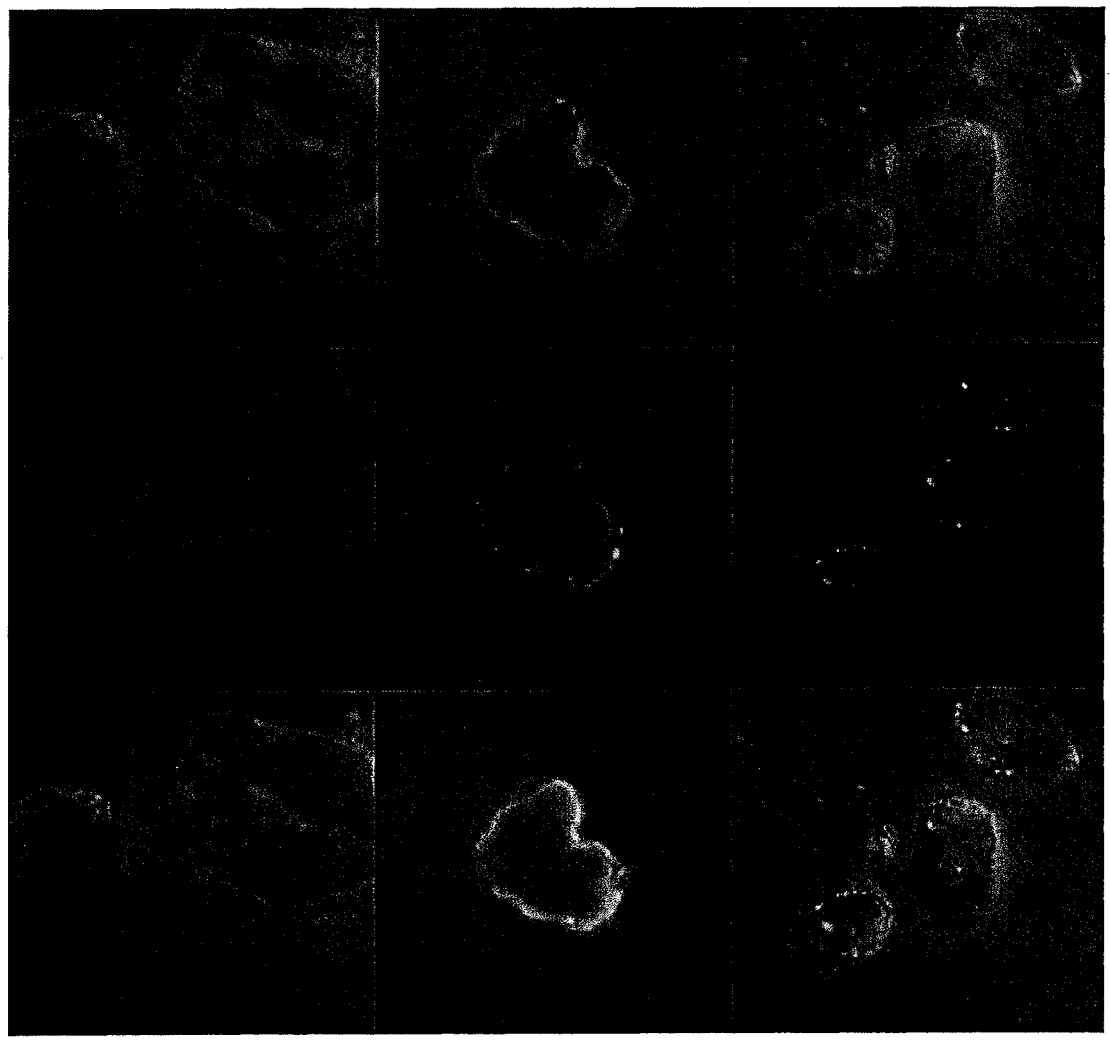
FIG. 6 shows the results of observing the distribution of a drug in cellulose acetate particles, using a fluorescent-labeled motilin derivative. Left column: Cellulose acetate powder; Center column: Composition of Example 10; Right column: Composition of Comparative Example 9; Top row: Transmitted light image; Center row: Fluorescent image; Bottom row: Combination of transmitted light image and fluorescent image.

The cellulose acetate and compositions prepared in Example 10 and Comparative Example 9 were observed under an LSM700 confocal microscope (Zeiss). The results are shown in FIG. 6. No fluorescence was observed in the cellulose acetate powder. Homogeneous fluorescence was observed inside the particles in the composition of Example 10. Granular fluorescence was also observed on the particle surfaces in the composition of Comparative Example 9. This indicated that when the composition is prepared using water, the drug penetrates to the interiors of the particles so that a composition comprising the bioactive substance in the particle interiors is obtained, whereas when water is not used, a composition with the bioactive substance adhering to the particle surfaces is obtained.

Cellulose acetate safety was investigated based on irritation of the nasal mucosa of cynomolgus monkeys using cellulose acetate. Cellulose acetate was nasally administered at 20 mg 3 times a day for 2 weeks, and the nasal mucosa were histologically observed. Abnormalities were not found in the nasal mucosa, indicating no problems in terms of safety.

Industrial Applicability

A composition comprising cellulose acetate as the base, according to the invention, increases the bioavailability of physiologically active peptides as active compounds, when atomized on the mucous membrane of the nasal cavity or inhaled. Consequently, the composition allows physiologically active peptides that have hitherto been supplied only in the form of injections, to be intranasally administered in painless form at home. Furthermore, since cellulose acetate has low water absorption, it can avoid the unpleasant feelings such as itchiness that are encountered when using a base with high water absorption such as crystalline cellulose, and a composition for nasal administration with excellent safety can be provided.

The invention claimed is:

1. A powdered composition for nasal administration comprising a physiologically active peptide and cellulose acetate as a base, wherein the composition is obtained by 1) mixing the physiologically active peptide, cellulose acetate and at least 20 wt % of water with respect to the cellulose acetate, and 2) drying the mixture,
wherein the physiologically active peptide is human glucagon-like peptide-1, human parathyroid hormone (hPTH), hPTH (1-34), human motilin, a human motilin derivative consisting of the amino acid sequence of SEQ ID NO: 1, human ghrelin, human atrial natriuretic peptide, brain natriuretic peptide (BNP) or C-type natriuretic peptide (CNP).

2. The composition according to claim 1, wherein the amount of water used in the mixture of the physiologically active peptide, cellulose acetate and water is at least 20 wt % and no greater than 250 wt % with respect to the cellulose acetate.

3. The composition according to claim 2, wherein the amount of water used in the mixture of the physiologically active peptide, cellulose acetate and water is at least 100 wt % and no greater than 250 wt % with respect to the cellulose acetate.

4. The composition according to claim 1, wherein an acetylation degree of the cellulose acetate is 32-40%.

5. A method for preparing a powdered composition for nasal administration, which comprises a physiologically active peptide and cellulose acetate as a base, wherein the method comprises 1) mixing a physiologically active peptide, cellulose acetate and at least 20 wt % of water with respect to the cellulose acetate, and 2) drying the mixture,
wherein the physiologically active peptide is human glucagon-like peptide-1, human parathyroid hormone (hPTH), hPTH (1-34), human motilin, a human motilin derivative consisting of the amino acid sequence of SEQ ID NO: 1, human gherlin, human atrail natriurectic peptide, brain natriurectic, peptide (BNP) or C-type natriuretic peptide (CNP).

6. The method according to claim 5, wherein the amount of water used in the mixture of the physiologically active peptide, cellulose acetate and water is at least 20wt % and no greater than 250 wt % with respect to the cellulose acetate.

7. The method according to claim 6, wherein the amount of water used in the mixture of the physiologically active peptide, cellulose acetate and water is at least 100 wt % and no greater than 250 wt % with respect to the cellulose acetate.

8. The method according to claim 5, wherein an acetylation degree of the cellulose acetate is 32-40%.

* * * * *